United States Patent
Slusher et al.

(10) Patent No.: US 10,849,915 B2
(45) Date of Patent: *Dec. 1, 2020

(54) METHODS FOR TREATING INFLAMMATORY BOWEL DISEASE USING PROSTATE SPECIFIC MEMBRANE ANTIGEN (PSMA) INHIBITORS

(71) Applicant: The Johns Hopkins University, Baltimore, MD (US)

(72) Inventors: Barbara Slusher, Kingsville, MD (US); Rana Rais, West Friendship, MD (US); Xuhang Li, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/190,792

(22) Filed: Nov. 14, 2018

(65) Prior Publication Data

US 2019/0076447 A1   Mar. 14, 2019

Related U.S. Application Data

(62) Division of application No. 15/502,009, filed as application No. PCT/US2015/044025 on Aug. 6, 2015, now Pat. No. 10,172,873.

(60) Provisional application No. 62/033,948, filed on Aug. 6, 2014.

(51) Int. Cl.
| | | |
|---|---|---|
| *A61K 31/662* | (2006.01) | |
| *A61K 31/194* | (2006.01) | |
| *A61K 9/00* | (2006.01) | |
| *A61K 9/02* | (2006.01) | |

(52) U.S. Cl.
CPC .......... *A61K 31/662* (2013.01); *A61K 9/0031* (2013.01); *A61K 9/0053* (2013.01); *A61K 9/02* (2013.01); *A61K 31/194* (2013.01)

(58) Field of Classification Search
CPC .................................................. A61K 31/662
See application file for complete search history.

(56) References Cited

U.S. PATENT DOCUMENTS

| | | | | |
|---|---|---|---|---|
| 9,988,407 B2 * | 6/2018 | Slusher | ................. | C07F 9/4465 |
| 10,172,873 B2 * | 1/2019 | Slusher | ................. | A61K 31/194 |
| 2007/0041934 A1 | 2/2007 | Bernell et al. | | |
| 2011/0064657 A1 | 3/2011 | Pomper | | |

FOREIGN PATENT DOCUMENTS

| | | |
|---|---|---|
| WO | WO 2009/070302 | 6/2009 |
| WO | WO 2013/144176 | 10/2013 |

OTHER PUBLICATIONS

U.S. Appl. No. 15/968,074, filed May 2018, Slusher; Barbara.*
Alex P, et al. Clc-5 Knockout Mice Exhibit Novel Immunomodulatory Effects and Are More Susceptible to Dextran Sulphate Sodium Induced Colitis. J Immunol 2010;184:3988-3996.
Alex P, et al. Distinct cytokine patterns identified from multiplex profiles of murine DSS and TNBS-induced colitis. Inflamm Bowel Dis 2009;15:341-352.
Barditch-Crovo, P, et al. Phase i/ii trial of the pharmacokinetics, safety, and antiretroviral activity of tenofovir disoproxil fumarate in human immunodeficiency virus-infected adults. Antimicrob Agents Chemother 2001;45:2733-2739.
Barditch-Crovo, P, et al. Anti-human immunodeficiency virus (HIV) activity, safety, and pharmacokinetics of adefovir dipivoxil (9-[2-(bis-pivaloyloxymethyl)-phosphonylmethoxyethyl]adenine) in HIV-infected patients. J Infect Dis 1997;176:406-413.
Barinka C, et al. Glutamate carboxypeptidase II in diagnosis an treatment of Neurologic disorders and prostate cancer. Curr Med Chem. 2012; 19(6): 856-870.
Colombel, JF, et al. Adalimumab for maintenance of clinical response and remission in patients with Crohn's disease: the CHARM trial. Gastroenterology 2007;132:52-65.
Cundy, KC, et al. Oral formulations of adefovir dipivoxil: in vitro dissolution and in vivo bioavailability in dogs. J Pharm Sci 1997;86:1334-1338.
Fakoury, M, et al. Inflammatory bowel disease: clinical aspects and treatments. Journal of Inflammation Research 2014; 7: 113-120.
Glocker, EO, et al. IL-10 and IL-10 receptor defects in humans. Ann. N.Y. Acad. Sci. 2011; 1246: 102-107.
Hamilton, MJ, et al. Update on biologic pathways in inflammatory bowel disease and their therapeutic relevance. J Gastroenterol 2012;47:1-8.
Hanauer, SB, et al. Maintenance infliximab for Crohn's disease: the ACCENT I randomised trial. Lancet 2002;359:1541-1549.
Harsanyi, K, et al. Synthesis of 2-phosphinoxidomethyl- and 2-phosphonom ethyl glutaric acid derivatives. Heteroatom Chem. 2005; 16: 562-565.
Kaser, A, et al. Inflammatory bowel disease. Annu Rev Immunol 2010;28:573-621.
Kirschner, B. Safety of azathioprine and 6-mercaptopurine an pediatric patients with inflammatory bowel disease. Gastroenterology 1998; 115: 813-821.
Kozuch, PL, et al. Treatment of inflammatory bowel disease: A review of medical therapy. World J Gastroenterol 2008;14:354-377.
Kuhn, R, et al. Intetleukin-10-deficient mice develop chronic enterocolitis. Cell 1993; 75: 263-274.
Lautenschlager, C, et al. Drug delivery strategies in the therapy of inflammatory bowel disease. Adv Drug Deliv Rev. 2014; 71:58-76.
Lawrance, IC. What is left when anti-tumour necrosis factor therapy in inflammatory bowel diseases fails? World J Gastroenterol 2014;20:1248-1258.
Lupold, S, et al. Identification and characterization of nuclease-stabalized RNA molecules that bind human prostate cancer cells via the prostate-specific membrane antigen. Cancer Reasearch 2002; 62: 4029-4033.

(Continued)

*Primary Examiner* — Svetlana M Ivanova
(74) *Attorney, Agent, or Firm* — Casimir Jones, S.C.; Jeffrey W. Childers

(57) ABSTRACT

Methods and compounds are disclosed for treating inflammatory bowel disease (IBD) by using Prostate Specific Membrane Antigen (PSMA) inhibitors.

3 Claims, 9 Drawing Sheets

(56) References Cited

OTHER PUBLICATIONS

Mesters, JR, et al. Structure of glutamate carboxypeptidase II, a drug target in neuronal damage and prostate cancer. EMBO J 2006;25:1375-1384.

Rais, R, et al. Bioanalytical method for evaluating the pharmacokinetics of the GCP-II inhibitor 2-phosphonomethyl pentanedioic acid (2-PMPA). J Pharm Biomed Anal 2014;88:162-169.

Regueiro, M, et al. Infliximab dose intensification in Crohn's disease. Inflamm Bowel Dis 2007;13:1093-1099.

Ristau BT, et al. The prostate-specific membrane antigen: Lessons and current clinical implications from 20 years of research. Urol Oncol 2013.

Robinson M, et al. Hydrolysis of the brain dipeptide N- acetyl-1-aspartyl-1-glutamate. J Bio Chem 1987; 262: 14498-14506.

Rojas, C, Frazier ST, Flanary J, Slusher BS. Kinetics and inhibition of glutamate carboxypeptidase II using a microplate assay. Analytical biochemistry 2002; 310(1): 50-54.

Sartor, RB. Mechanisms of disease: pathogenesis of Crohn's disease and ulcerative colitis. Nat Clin Pract Gastroenterol Hepatol 2006;3:390-407.

Schmidt, C, et al. Predictive value of mucosal TNF-alpha transcripts in steroid-refractory Crohn's disease patients receiving intensive immunosuppressive therapy. Inflamm Bowel Dis 2007;13:65-70.

Schreiber, S, et al. Maintenance therapy with certolizumab pegol for Crohn's disease. N Engl J Med 2007;357:239-250.

Strober, W, et al. The fundamental basis of inflammatory bowel disease. J Clin Invest 2007;117:514-521.

Tang, H, et al. Prostate targeting ligands based on n-acetylated alpha-linked acidic dipeptidase. Biochem Biophys Res Commun. 2003; 307(1): 8-14.

Thackaberry, EA. Vehicle selection for nonclinical oral safety studies. Expert Opin Drug Metab Toxicol 2013;9:1635-1646.

Van AG, et al. Progressive multifocal leukoencephalopathy after natalizumab therapy for Crohn's disease. N Engl J Med 2005;353:362-368.

Wozniak et al: "The Orally Active Glutamate Carboxypeptidase II Inhibitor E2072 Exhibits Sustained Nerve Exposure and Attenuates Peripheral Neuropathy", Journal of Pharmacology and Experimental Therapeutics,vol. 343, No. 3, Dec. 1, 2012, pp. 746-754.

Xavier, RJ, et al. Unravelling the pathogenesis of inflammatory bowel disease. Nature 2007;448:427-434.

Zhang, T, et al. An ileal Crohn's disease gene signature based on whole human genome expression profiles of disease unaffected ileal mucosal biopsies. PLoS One 2012;7:e37139.

European Patent Office Extended Search Report for Application No. 15829737.4 dated Mar. 12, 2018 (6 pages).

International Search Report and Written Opinion for Application No. PCT/US2015/044025 dated Nov. 19, 2015 (4 pages).

\* cited by examiner

METHODS FOR TREATING INFLAMMATORY BOWEL DISEASE USING PROSTATE SPECIFIC MEMBRANE ANTIGEN (PSMA) INHIBITORS

CROSS-REFERENCE TO RELATED APPLICATIONS

This application is a divisional of U.S. patent application Ser. No. 15/502,009, filed Feb. 6, 2017, now allowed, which is a U.S. § 371 National Entry Application of International Patent Application No. PCT/US2015/044025, filed Aug. 6, 2015, which claims the benefit of U.S. Provisional Application No. 62/033,948, filed Aug. 6, 2014, each of which is incorporated herein by reference in its entirety.

FEDERALLY SPONSORED RESEARCH OR DEVELOPMENT

This invention was made with government support under CA161056 awarded by the National Institutes of Health. The government has certain rights in the invention.

BACKGROUND

Inflammatory Bowel Disease (IBD), an idiopathic, chronic and frequently disabling inflammatory disorder of the intestine, has two subtypes: Crohn's disease (CD) and ulcerative colitis (UC), each accounting for approximately 50% of IBD patients (Xavier and Podolsky, 2007; Srober et al., 2007; Sartor, 2006). IBD is a widespread GI disease, with a prevalence of approximately 0.2% in the Western population. In the United States alone, there are 1.4 million diagnosed IBD patients, resulting in enormous suffering and health-care costs. It is increasingly clear that IBD is a complex multifactorial disease with both genetic and environmental contributions, the interaction of which leads to IBD (Xavier and Podolsky; Strober et al., 2007; Sartor, 2006; Kaser et al., 2010). Unfortunately, the etiology of this mucosal dysregulation in UC and CD remain elusive (Kaser et al., 2010). Despite increasing therapeutic options available for the management of IBD, approximately ⅓ of IBD patients do not respond to any given therapy, and there is no cure for IBD (Hamilton et al., 2012). Anti-tumor necrosis factor (TNF)-based therapies, such as infliximab (IFX), adalimumab and certolizumab pegol are currently the most effective therapies for severe UC and CD (Hanauer et al., 2002; Kozuch and Hanauer, 2008; Colombel et al., 2007; Schreiber et al., 2007). However, one-third of patients with CD do not respond to anti-TNF therapies and another third lose responsiveness within six months of initiating therapy (Regueiro et al., 2007; Lawrance, 2014). These non-responders have more aggressive mucosal immune responses and additional treatments are indicated (Schmidt et al., 2007). Patients with extensive disease or who are at risk for short gut syndrome due to prior resections are usually poor surgical candidates. Currently, the only approved medication for patients who have failed an anti-TNF agent is natalizumab. However, natalizumab has been associated with several cases of progressive and often fatal multifocal leukoencephalopathy (PML) (Van et al., 2005). This emphasizes the significance of exploring and identifying new and more effective therapies in patients with IBD.

SUMMARY

In one aspect, the presently disclosed subject matter provides a method for treating an inflammatory bowel disease (IBD) in a subject in need thereof, the method comprising administering to the subject a therapeutically effective amount of a Prostate Specific Membrane Antigen (PSMA) inhibitor.

In a particular aspect, the PSMA inhibitor for use in the methods of the presently disclosed subject matter is 2-(phosphonomethyl)-pentanedioic acid (2-PMPA), having the structure:

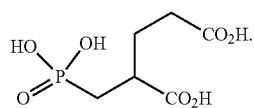

In further aspects, the IBD is selected from the group consisting of Crohn's disease (CD) and ulcerative colitis (UC), and the 2-PMPA is administered parenterally.

In another particular aspect, the PSMA inhibitor for use in the methods of the presently disclosed subject matter is (3-2-Mercaptoethyl)biphenyl-2,3-dicarboxylic acid (E2072), having the structure:

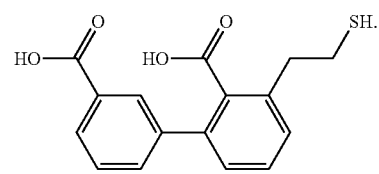 [SMILES: O=C(O)c1cccc(-c2cccc(CCS)c2C(=O)O)c1]

In further aspects, the IBD is selected from the group consisting of CD and UC, and the E2072 is administered parenterally.

In another particular aspect, the PSMA inhibitor for use in the methods of the presently disclosed subject matter is an ester prodrug of 2-PMPA (e.g. a phosphonate or carboxylate prodrug of 2-PMPA), wherein acidic moieties in the ester prodrug have been capped with pivaloyloxymethyl (POM) or propyloxycarbonyloxymethyl (POC). In yet another particular aspect, the ester prodrug of 2-PMPA is Tris-propyloxycarbonyloxymethyl-2-(phosphonomethyl)-pentanedioic acid (Tris-POC-2-PMPA), having the structure:

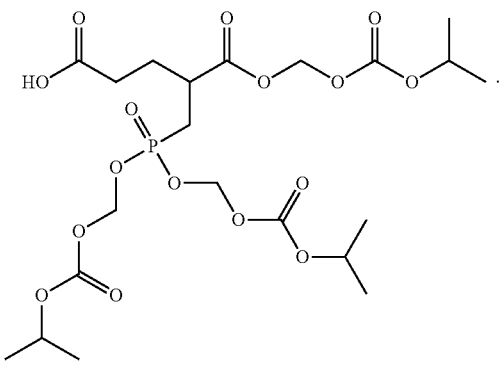 [SMILES: CC(C)OC(=O)OCOC(=O)C(CCC(=O)O)CP(=O)(OCOC(=O)OC(C)C)OCOC(=O)OC(C)C]

In further aspects, the IBD is selected from the group consisting of CD and UC, and the ester prodrug of 2-PMPA is administered orally. In further aspects, the IBD is selected from the group consisting of CD and UC, and the Tris-POC-2-PMPA is administered orally. In further aspects, the IBD is selected from the group consisting of CD and UC, and the ester prodrug of 2-PMPA is administered via a suppository. In further aspects, the IBD is selected from the group consisting of CD and UC, and the Tris-POC-2-PMPA is administered via a suppository. In some embodiments, the suppository is a rectal suppository.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figures 1A, 1B:
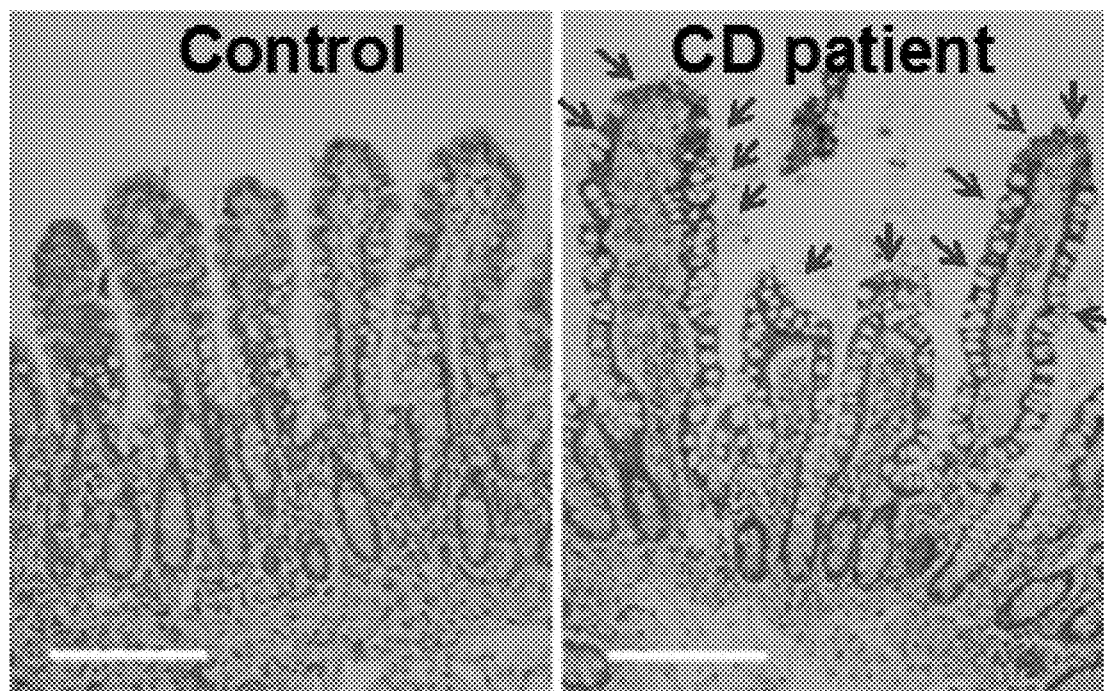
Figure 2A:
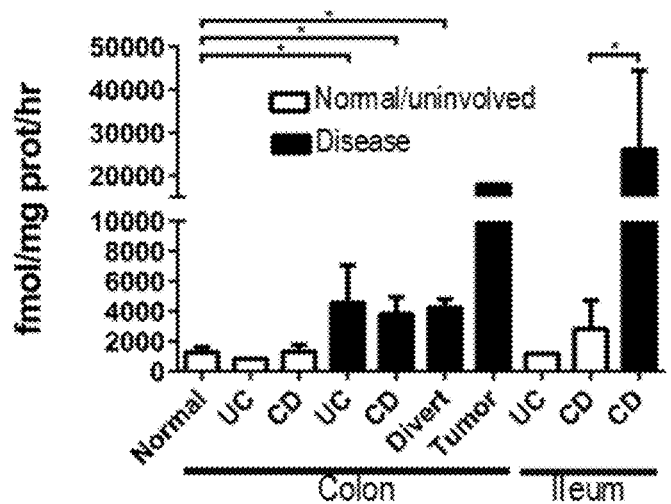
Figure 2B:
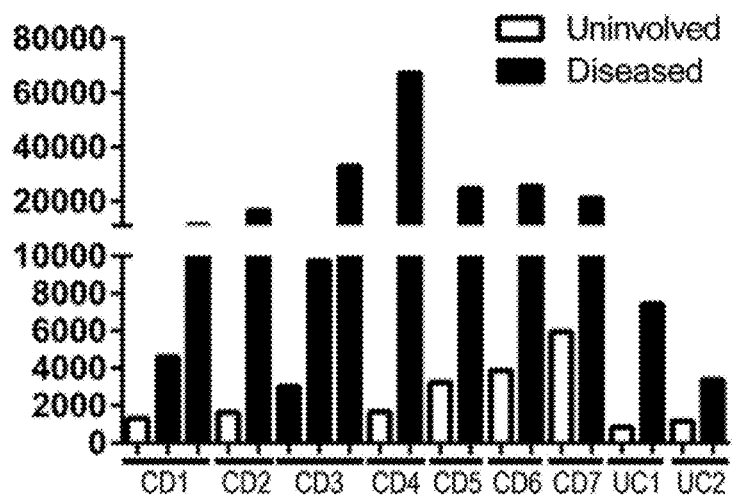
Figure 3:
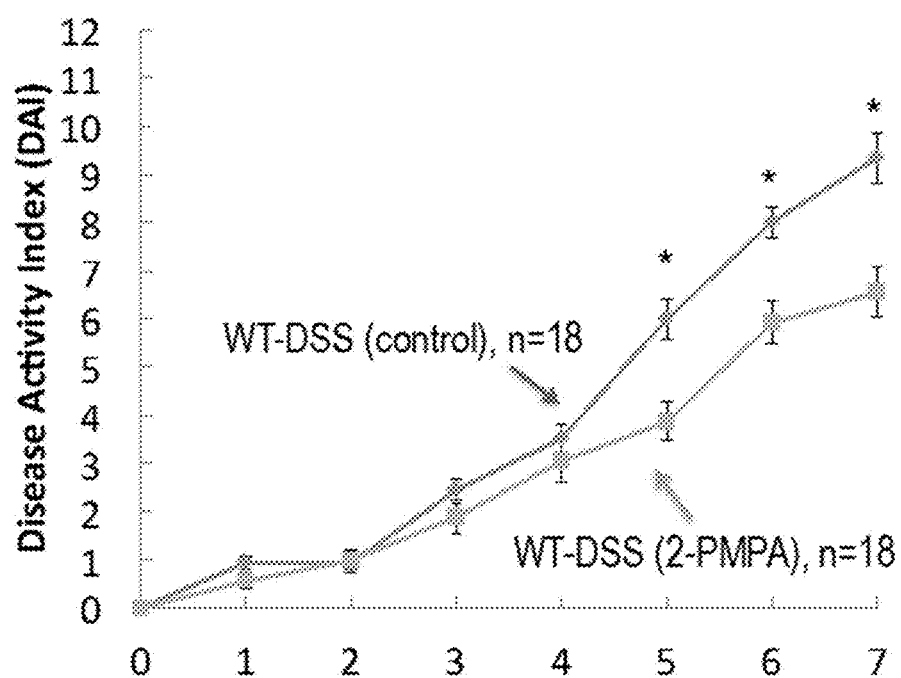
Figure 4:
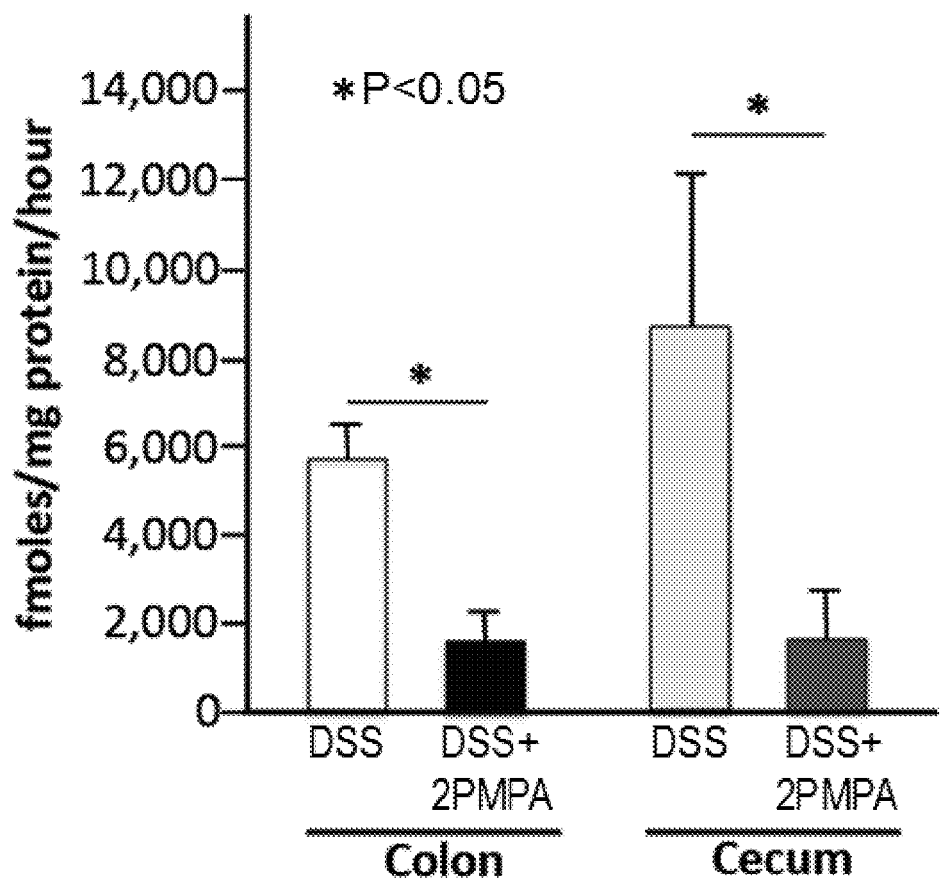
Figure 5:
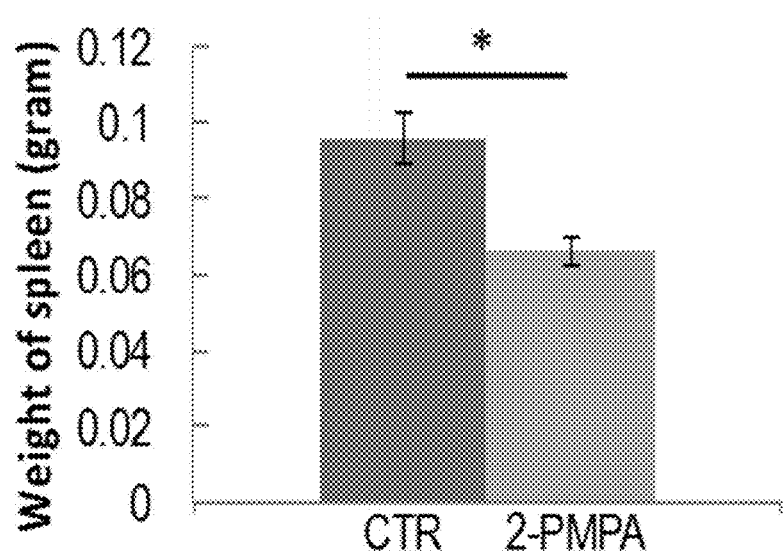
Figure 7:
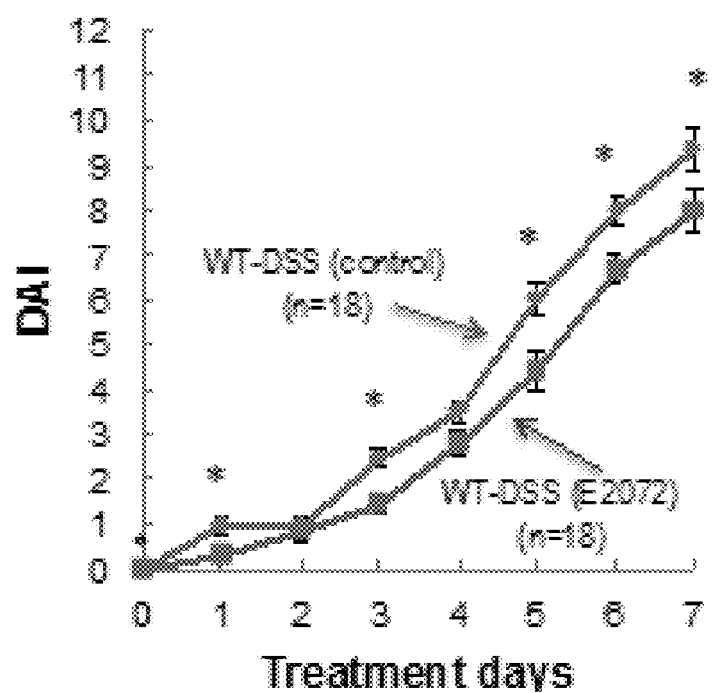
Figure 8A:
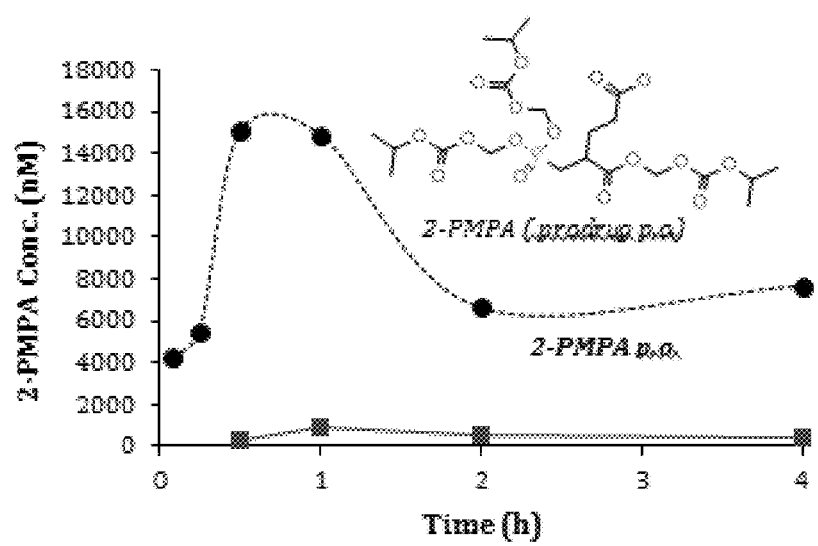
Figure 8B:
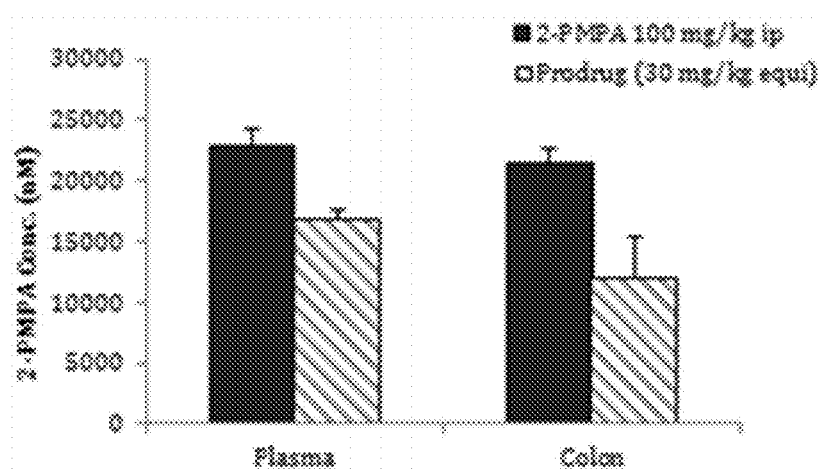
Figure 9:
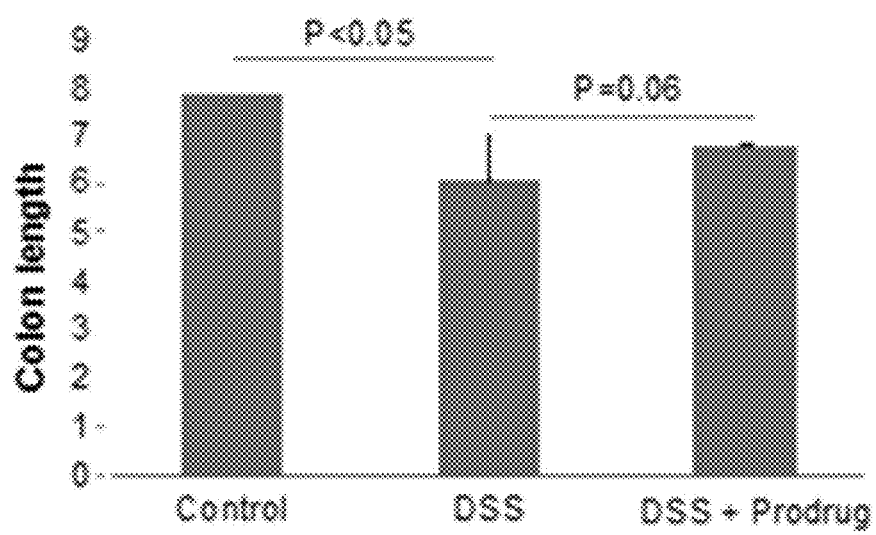

Having thus described the presently disclosed subject matter in general terms, reference will now be made to the accompanying Figures, which are not necessarily drawn to scale, and wherein:

FIG. 1A and FIG. 1B show the marked increase of PSMA expression in the villous epithelium from ileal sample of CD patient (Zhang et al., 2012). Immunohistochemical localization of PSMA (indicated by arrows) in: (FIG. 1A) control non-IBD subject; and (FIG. 1B) diseased ileal mucosa from the proximal margin of resected ileum from an ileal CD subject. Magnification is 100×. Bar is 200 mm;

FIG. 2A and FIG. 2B show the marked elevation of PMSA activity in the inflamed (disease) intestinal mucosa of patients with IBD. PMSA activity was measured from mucosa specimens from involved (inflamed with active disease) and uninvolved (macroscopically normal, as a control) from IBD patients or from non-IBD controls (healthy controls or patients with diverticulitis) (n=20): (FIG. 2A) comparison between IBD (active disease vs. normal/uninvolved tissues) vs. non-IBD controls; and (FIG. 2B) comparison between active disease vs. normal/uninvolved of the same patients (CD, Crohn's disease; UC, ulcerative colitis; the Arabic numbers refer to different patients). Note: GCPII is also highly upregulated in colon cancer (see A). *P<0.05;

FIG. 3 shows that PSMAi (2-PMPA) ameliorates disease activity in DSS-induced murine model of colitis. C57/B6 mice (approximately 8 weeks old) that were induced to develop colitis with DSS (2.5%, 7 days in drinking water) were treated simultaneously with the vehicle or 2-PMPA (100 mg/kg), respectively. Disease activity index (DAI), which positively correlated with the disease severity, was used as a measure for clinical activity. *P<0.05;

FIG. 4 shows that PSMAi (2-PMPA) effectively suppresses PSMA activity in the colonic or cecal mucosa of DSS-induced murine model of colitis. PSMA activity was measured using extract from mucosa;

FIG. 5 shows that 2-PMPA treatment reduces size and weight of spleen DSS-induced murine model of colitis;

FIG. 6A, FIG. 6B, FIG. 6C, and FIG. 6D show that PSMAi (2-PMPA) treatment leads to not only improvement of disease but even retraction of prolapse in IL-10 knockout (IL-10 KO) mice that spontaneously develop colitis. IL-10 KO mice (C57/B6; 3 month old) were treated with 2-PMPA (100 mg/kg) for 2 weeks: (FIG. 6A) improvement of prolapse and colonic macroscopic disease (inflammation, hypertrophy, stool inconsistency); (FIG. 6B) colon weight changes; (FIG. 6C) body weight after 2-PMPA; and (FIG. 6D) prolapse retraction after treatment. *P<0.05;

FIG. 7 shows that E2072, a PSMAi that is structurally distinct from 2-PMPA, also ameliorates disease activity in DSS-induced murine model of colitis. Experiments were performed as described in FIG. 3. Disease activity index (DAI), which positively correlated with the disease severity, was used as a measure for clinical activity. *P<0.05;

FIG. 8A and FIG. 8B show orally available Tris POC 2-PMPA prodrug: (FIG. 8A) plasma 2-PMPA concentrations following 30 mg/kg per oral administration of 2-PMPA (red squares) or 2-PMPA prodrug (black circles). 2-PMPA prodrug achieved 20-30-fold enhancements in permeability; and (FIG. 8B) comparison of plasma and colonic 2-PMPA concentrations following 100 mg/kg i.p. administration of 2-PMPA (red bars) or 2-PMPA prodrug (blue bars). 2-PMPA prodrug achieved concentrations similar to 2-PMPA i.p. dose which was efficacious in both DSS and IL-10 knockout models; and FIG. 9 shows that prodrug Tris POC 2-PMPA treatment reverses the colon shortening of DSS colitis mice. The p value (P-0.06) was close but did not reach statistic significance, at least in part due to the small number of mice in each group (n=5 per group).

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw- Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

Immune-mediated gastrointestinal disorders encompass a wide range of debilitating gastrointestinal diseases of various etiologies. One such immune-mediated gastrointestinal disorder, inflammatory bowel disease (IBD), is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. The onset of IBD typically occurs during young adulthood, with the most common symptoms being diarrhea, abdominal pain, and fever. The diarrhea may range from mild to severe and in ulcerative colitis often is accompanied by bleeding. Anemia and weight loss are additional common signs of IBD. Ten percent to fifteen percent of all patients with IBD will require surgery over a ten year period. In addition, patients with IBD are at increased risk for the development of intestinal cancer. Increased occurrence of psychological problems, including anxiety and depression, are perhaps not surprising symptoms of what is often a debilitating disease that strikes people in the prime of life.

6-Mercaptopurine (6-MP) and azathioprine (AZA), a prodrug that is non-enzymatically converted to 6-mercaptopurine (6-MP), are 6-MP drugs that have been used as treatments for inflammatory bowel diseases such as Crohn's disease and ulcerative colitis (Kirschner, 1998). 6-MP can be enzymatically converted to various 6-MP metabolites, including 6-methyl-mercaptopurine (6-MMP) and 6-thioguanine (6-TG) and their nucleotides. 6-TG nucleotides are thought to be the active metabolite in mediating many of the effects of 6-MP drug treatment.

Thiopurine methyltransferase (TPMT) is a cytoplasmic enzyme that preferentially catalyzes the S-methylation of 6-MP and 6-TG to form S-methylated metabolites such as 6-MMP and 6-methylthioguanine (6-MTG), respectively. TPMT exhibits genetic polymorphism, with 89% of Caucasians and African Americans having high activity, 11% intermediate activity and 1 in 300 TPMT deficient. Clinical studies with AZA and 6-MP have shown an inverse relationship between TPMT activity and 6-TGN accumulation. Patients who less efficiently methylate these thiopurines have more extensive conversion to 6-TGN, which can lead to potentially fatal hematopoietic toxicity. Therefore, patients who have less active TPMT can be more susceptible to toxic side effects of 6-MP therapy.

Although drugs such as 6-MP and AZA have been used for treating IBD, non-responsiveness and drug toxicity unfortunately have complicated treatment in some patients. Complications associated with 6-MP drug treatment include allergic reactions, neoplasia, opportunistic infections, hepatitis, bone marrow suppression, and pancreatitis. Therefore, many physicians are reluctant to treat patients with AZA because of its potential side effects, especially infection and neoplasia.

Anti-tumor necrosis factor (TNF)-based therapies, such as infliximab (IFX), adalimumab and certolizumab pegol are currently the most effective therapies for severe UC and CD (Hanauer et al., 2002; Kozuch and Hanauer, 2008; Colombel et al., 2007; Schreiber et al., 2007). Despite increasing therapeutic options available for the management of IBD, approximately ⅓ of IBD patients do not respond to any given therapy, and there is no cure for IBD (Hamilton et al., 2012). For example, one-third of patients with CD do not respond to anti-TNF therapies and another third lose responsiveness within six months of initiating therapy (Regueiro et al., 2007; Lawrance, 2014). These non-responders have more aggressive mucosal immune responses and additional treatments are indicated (Schmidt et al., 2007). Patients with extensive disease or who are at risk for short gut syndrome due to prior resections are usually poor surgical candidates. Currently, the only approved medication for patients who have failed an anti-TNF agent is natalizumab. However, natalizumab has been associated with several cases of progressive and often fatal multifocal leukoencephalopathy (PML) (Van et al., 2005). This emphasizes the significance of exploring and identifying new and more effective therapies in patients with IBD.

As described more fully in the Examples below, the presently disclosed subject matter relates to the discovery that Prostate Specific Membrane Antigen (PSMA) enzymatic activity is consistently and robustly activated in human IBD, and that pharmacological inhibition of PSMA using multiple structurally distinct inhibitors ameliorate IBD symptoms in two murine preclinical models.

I. Methods of Treating Inflammatory Bowel Disease with a Prostate Specific Membrane Antigen Inhibitor In one embodiment, the presently disclosed subject matter provides a method for treating Inflammatory Bowel Disease (IBD) in a subject in need thereof with a therapeutically effective amount of a Prostate Specific Membrane Antigen (PSMA) inhibitor.

PSMA, also termed Glutamate Carboxypeptidase II (GC-PII) and Folate Hydrolase I (FOLH1), is a metallopeptidase that catalyzes the hydrolysis of N-acetylated aspartate-glutamate (NAAG) to N-acetyl aspartate (NAA) and glutamate and cleaves terminal glutamate moieties sequentially from folate polyglutamate (Ristau et al., 2013; Mesters et al., 2006; Slusher et al., 2013). As used herein, the terms "PSMA" or "PSMA polypeptide" refer to a naturally occurring or endogenous PSMA and to proteins having an amino acid sequence which is the same as that of a naturally occurring or endogenous PSMA (e.g., recombinant proteins). Accordingly, as defined herein, the term includes mature PSMA, glycosylated or unglycosylated PSMA proteins, polymorphic or allelic variants, and other isoforms of PSMA (e.g., produced by alternative splicing or other cellular processes).

As used herein, a PSMA inhibitor is a molecule that decreases or inhibits the activity of PSMA. The modulation of the activity of PSMA may be detected by use of an assay for the intrinsic N-acetylated alpha-linked acidic dipeptidase (NAALADase) activity of PSMA (Tang et al., 2003; Robinson et al., 1987; Lupold et al., 2002; U.S. Patent App. Pub. No. 20110064657). Inhibition curves may be determined using semi-log plots and $IC_{50}$ values determined at the concentration at which enzyme activity was inhibited by 50%. In some embodiments, the PSMA inhibitor has an $IC_{50}$ value ranging from about 0.1 to about 200 nM. In a further embodiment, the PSMA inhibitor has an $IC_{50}$ value ranging from about 0.5 to about 118 nM.

The PSMA inhibitor may interact with PSMA directly (e.g., via interaction with the binding site of PSMA) or may interact with another molecule that results in a decrease in the activity of PSMA. The binding site of PSMA contains a binuclear zinc ion and two substrate binding pockets, i.e., an S1 (nonpharmacophore) pocket and an S1' (pharmacophore) pocket. The active site also contains a chloride ion in the S1 pocket. In the vicinity of the S1 pocket resides a funnel-shaped tunnel with a depth of approximately 20 Å and a width of 8-9 Å. Similarly, a narrow cavity is present near the S1' pocket.

In one embodiment, the PSMA inhibitor for use within the methods of the presently disclosed subject matter is 2-(phosphonomethyl)-pentanedioic acid (2-PMPA), having the structure:

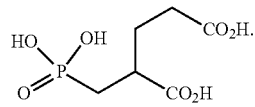

In another embodiment, the PSMA inhibitor for use within the methods of the presently disclosed subject matter is (3-2-Mercaptoethyl)biphenyl-2,3-dicarboxylic acid (E2072), having the structure:

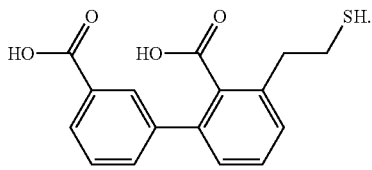

In another embodiment, the PSMA inhibitor for use within the methods of the presently disclosed subject matter is an ester prodrug of 2-PMPA (e.g. a phosphonate or carboxylate prodrug of 2-PMPA) wherein acidic moieties have been capped with pivaloyloxymethyl (POM) or propyloxycarbonyloxymethyl (POC). Non-limiting examples of ester prodrugs of 2-PMPA of use herein are described in international PCT Application PCT/US2015/044053 entitled "Prodrugs of PSMA Inhibitor", which is herein incorporated by reference in its entirety. In one embodiment, the ester prodrug of 2-PMPA is Tris-propyloxycarbonyloxymethyl-2-(phosphonomethyl)-pentanedioic acid (Tris-POC-2-PMPA), having the structure:

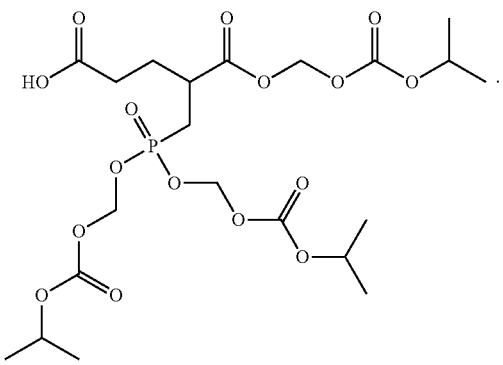 [SMILES: CC(C)OC(=O)OCOC(=O)C(CCC(=O)O)CP(=O)(OCOC(=O)OC(C)C)OCOC(=O)OC(C)C]

As described more fully in the Examples below, there is a marked elevation of PMSA activity in the diseased intestinal mucosa of subjects with IBD. As used herein, the term "elevated PSMA activity" means an increase of PSMA activity in a subject with IBD as compared to the PSMA activity in a subject without IBD, such as an increase of approximately 100%, 200%, 300%, 400%, 500%, 600%, 700%, 800%, 900%, 1000%, or more.

In some embodiments, the presently disclosed subject matter provides methods for inhibiting PMSA activity in a subject with IBD. As used herein, the term "inhibit" means to decrease or diminish PSMA activity in a subject in need thereof. The term "inhibit" also may mean to decrease, suppress, attenuate, diminish, arrest, or stabilize the development or progression of a disease or condition, such as IBD. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder.

In general, using the presently disclosed methods to treat the IBD in a subject results in a decrease in the severity of the IBD. As used herein, the terms "treat," "treating," "treatment," and the like refer to reducing or ameliorating a disease or condition, such as IBD, and/or symptoms associated therewith. It will be appreciated that, although not precluded, treating a disease or condition, such as IBD, does not require that the disorder, condition or symptoms associated therewith be completely eliminated. The term "decrease" is meant to inhibit, suppress, attenuate, diminish, arrest, or stabilize at least one symptom of IBD (e.g., rectal prolapse, gut inflammation, colonic hypertrophy, stool inconsistency, and the like).

IBD has been classified into the broad categories of Crohn's disease and ulcerative colitis. Accordingly, as used herein, "a subject having inflammatory bowel disease" is synonymous with the term "a subject diagnosed with having an inflammatory bowel disease," and means a patient having Crohn's disease or ulcerative colitis. Crohn's disease (regional enteritis) is a disease of chronic inflammation that can involve any part of the gastrointestinal tract. Commonly, the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also includes complications such as inflammation of the eye, joints and skin; liver disease; kidney stones or amyloidosis. In addition, CD is associated with an increased risk of intestinal cancer.

Several features are characteristic of the pathology of Crohn's disease. The inflammation associated with CD, known as transmural inflammation, involves all layers of the bowel wall. Thickening and edema, for example, typically also appear throughout the bowel wall, with fibrosis also present in long-standing disease. The inflammation characteristic of CD also is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. Some Crohn's disease cases display the typical discrete granulomas, while others show nonspecific transmural inflammation. As a result, the presence of discrete granulomas is indicative of CD, although the absence of granulomas also is consistent with the disease. Thus, transmural or discontinuous inflammation, rather than the presence of granulomas, is a preferred diagnostic indicator of Crohn's disease (Rubin and Farber, 1994).

Ulcerative colitis (UC) is a disease of the large intestine characterized by chronic diarrhea with cramping abdominal pain, rectal bleeding, and loose discharges of blood, pus and mucus. The manifestations of ulcerative colitis vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. The inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerated intestinal crypts are filled with neutrophils, also are typical of ulcerative colitis (Rubin and Farber, 1994).

In comparison with Crohn's disease, which is a patchy disease with frequent sparing of the rectum, ulcerative colitis is characterized by a continuous inflammation of the colon that usually is more severe distally than proximally. The inflammation in ulcerative colitis is superficial in that it is usually limited to the mucosal layer and is characterized by an acute inflammatory infiltrate with neutrophils and crypt abscesses. In contrast, Crohn's disease affects the entire thickness of the bowel wall with granulomas often, although not always, present. Disease that terminates at the ileocecal valve, or in the colon distal to it, is indicative of ulcerative colitis, while involvement of the terminal ileum, a cobblestone-like appearance, discrete ulcers or fistulas suggest Crohn's disease.

II. Pharmaceutical Compositions and Administration

In another aspect, the present disclosure provides a pharmaceutical composition including a PSMA inhibitor alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the PSMA inhibitor for use within the methods of the presently disclosed subject matter can be formulated for a variety of modes of administration, including oral, systemic, and topical or localized administration. Techniques and formulations generally may be found in Remington: The Science and Practice of Pharmacy ($20^{th}$ ed.) Lippincott, Williams & Wilkins (2000).

In one embodiment, where the PSMA inhibitor for use within the methods of the presently disclosed subject matter is an ester prodrug of 2-PMPA wherein acidic moieties have been capped with pivaloyloxymethyl (POM) or propyloxycarbonyloxymethyl (POC), the PSMA inhibitor is formulated for oral administration. In a particular embodiment, the PSMA inhibitor formulated for oral administration for use within the methods of the presently disclosed subject matter is Tris-POC-2-PMPA. In a particular embodiment, the PSMA inhibitor is formulated for administration via a suppository. In a particular embodiment, the PSMA inhibitor formulated for administration via a suppository is Tris-POC-2-PMPA. In some embodiments, the suppository is a rectal suppository. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000).

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

In another embodiment, where the PSMA inhibitor for use within the methods of the presently disclosed subject matter is 2-PMPA or E2072, the PSMA inhibitor may be formulated into liquid or solid dosage forms and administered systemically or locally. Suitable routes may include rectal (e.g., via a suppository), intestinal, or intraperitoneal delivery. Other suitable routes may include various forms of parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Additional therapeutic agents, which are normally administered to treat or prevent IBD, may be administered together with the PSMA inhibitors within the methods of the presently disclosed subject matter. For example, anti-tumor necrosis factor (TNF)-based therapies, such as infliximab (IFX), adalimumab and certolizumab pegol, may be combined with the PSMA inhibitors of this disclosure to treat IBD.

Other examples of agents with which the disclosed PSMA inhibitors may also be combined include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors, such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

III. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to PSMA inhibitors are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$<sub>S</sub>—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, 0-$CH_3$, -0-$CH_2$—$CH_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a C$_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched C$_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

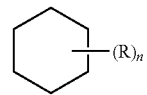

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

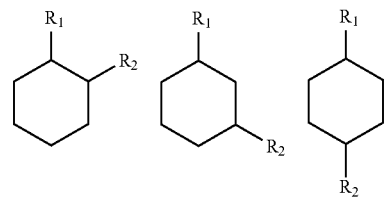

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⁓⁓⁓⁓ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C═O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

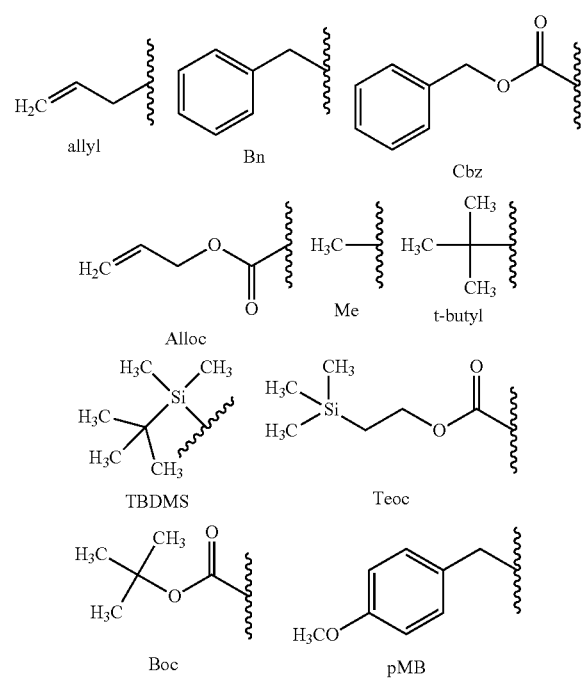

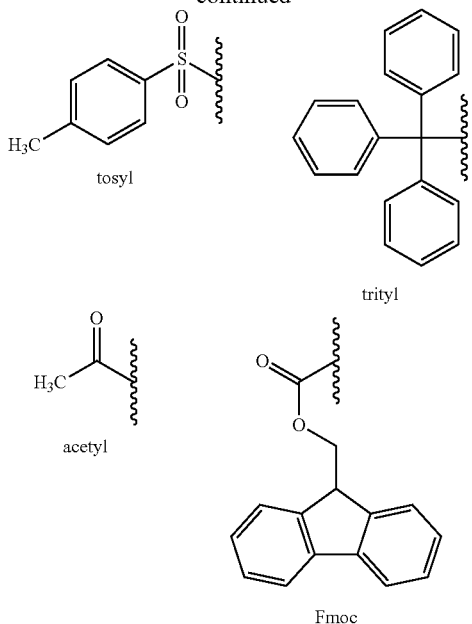

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods

Murine Models of IBD: IL-10 Knockout (KO) and DSS-Induced Colitis.

DSS-induced colitis model was generated as described previously (Alex et al., 2009; Alex et al., 2010). IL-10-KO mice, generated by gene-targeting, exhibited spontaneous colitis when maintained in H. polyri-positive condition, is one of the most widely used and most relevant murine models of colitis, was described in details previously (Kuhn et al., 1993). The fact that mutations in either IL-10 or IL-10 receptors in human lead to spontaneous Crohn's disease at very early age (usually less than 1 year old) (Glocker et al., 2011), further emphasize the critical role of IL-10 signaling pathway in its anti-inflammatory and immune-modulatory effects in the gut and the homeostasis of healthy gut.

Bioanalysis of 2-PMPA:

Blood and colonic mucosa were collected for drug PK analysis. Plasma was generated from blood by centrifugation and all samples were stored at −80° C. until further analysis. Concentrations of inhibitors in plasma and tissue were determined via LC/MS/MS as described previously (Rais et al., 2013). Briefly, 2-PMPA was extracted from plasma and tissue by protein precipitation with 5× methanol containing 2-(phosphonomethyl) succinic acid (2-PMSA; 1 μM) as an internal standard. The samples were vortexed (30 s) and centrifuged (10,000 g for 10 min). Supernatant was dried under a gentle stream of nitrogen at 45° C. and the residue was reconstituted with 100 μL of acetonitrile and vortexed. 50 μL of derivatizing agent N-tert-Butyldimethysilyl-N-methyltrifluoro-acetamide (MTBSTFA) was added to microcentrifuge tubes, vortexed, and heated at approximately 60° C. for 40 min. At the end of 40 min, the derivatized samples were analyzed via LC/MS/MS. Chromatographic analysis was performed using an Accela™ ultra high-performance system consisting of an analytical pump, and an autosampler coupled with TSQ Vantage mass spectrometer (Thermo Fisher Scientific Inc., Waltham Mass.). Separation of the analyte from potentially interfering material was achieved at ambient temperature using Waters X-terraR, RP18, 3.5 μm, and (2.1×50 mm). The mobile phase used was composed of 0.1% formic acid in acetonitrile and 0.1% formic acid in $H_2O$ with gradient elution, starting with 90% (organic) linearly increasing to 99% up to 2.5 min, maintaining at 99% (2.5-4.0 min) and reequilibrating to 90% by 5 min. The total run time for each analyte was 5.0 min. The [M+H]+ ion transitions of derivatized 2-PMPA at m/z 683.0>551.4 and that of the internal standard at m/z 669.0>537.2 were monitored with the total run time of 5 min.

GCPII Ex Vivo Activity Assay:

On the day of the ex vivo experiment, the tissues were weighed and immersed in 0.5 ml of ice-cold 50 mM Tris Buffer (pH 7.7 at RT). While on ice, each tissue was sonicated for 30-60 seconds (medium output, 60) via use of a Kontes Ultrasonic Cell Disrupter. After a 2 min spin at 13,000 rpm, supernatants were analyzed for protein content (Dc Protein Assay Kit; Bio Rad). NAAG-hydrolyzing activity measurements were carried out, based on published procedures Robinson et al., 1987; Rojas et al., 2002). Briefly, the reaction mixture (total volume of 50 μL) contained NAA[3H]G (70 nM, 50 Ci/mmol) and tissue lysates (7 concentrations each, tested in quadruplicate), in Tris-HCl (pH 7.4, 40 mM) containing 1 mM $CoCl_2$. Assay standards were comprised of human recombinant GCPII enzyme (40-200 pM, final). The reaction was carried out at 37° C. for 40-45 min and stopped with ice-cold sodium phosphate buffer (pH 7.4, 0.1 M, 50 μL). Blanks were obtained by incubating the reaction mixture in the absence of enzyme source. A 90 μL aliquot from each terminated reaction was transferred to a well in a 96-well spin column containing AG1X8 ion-exchange resin; the plate was centrifuged at 1500 rpm for 5 min using a Beckman GS-6R centrifuge equipped with a PTS-2000 rotor. NAA[3H]G bound to the resin and [3H]-G eluted in the flow through. Columns were then washed twice with formate (1 M, 90 µL) to ensure complete elution of [3H]-G. The flow through and the washes were collected in a deep 96-well block; from each well with a total volume of 270 µL, a 200 µL aliquot was transferred to its respective well in a solid scintillator-coated 96-well plate (Packard) and dried to completion. The radioactivity corresponding to [3H]-G was determined with a scintillation counter (Topcount NXT, Packard, counting efficiency 80%). Enzymatic activity (fmol/mg total protein/hour) determinations were based on slopes of lines obtained from CPM→DPM→molar conversion per unit time vs protein concentrations. Results were generated via use of Microsoft Office Excel 2007 and GraphPad Prism 5 programs.

Example 2

PSMA Expression and Enzymatic Activity is Selectively Elevated in Patient Samples with IBD Previously gene-profiling and immuno-histological analyses (FIG. 1A and FIG. 1B) showed that PSMA is significantly upregulated in the intestinal mucosa of patients with Crohn's disease (Zhang et al., 2012). To further determine the relevance of PSMA to IBD, PSMA functional enzymatic activity was examined in normal and diseased mucosa of 32 surgical intestinal specimens from 20 subjects (FIG. 2A and FIG. 2B), including healthy controls, patients with IBD, and non-IBD controls (diverticulitis). A very significant and robust 300-1,000% increase in PSMA activity was found in the intestinal mucosa with active IBD when compared to that in an uninvolved area of the same patients, or the intestine from healthy and non-IBD controls. These data suggest a clear positive association between activation of PSMA and IBD.

Example 3

Preclinical Efficacy: 2-PMPA, a Potent and Selective PSMA Inhibitor (PSMAi), Shows Profound Efficacy in Two Major Animal Models of IBD To investigate whether PSMA can be a suitable novel therapeutic target for clinical intervention against IBD, the effect of PSMA prototype inhibitors on two most widely used murine models of IBD, DSS-induced colitis, and IL-10 knockout (IL-10 KO) mice (a genetic model that develops spontaneous colitis), was tested. In both models, PSMA inhibitor treatment dramatically ameliorated symptoms. In the DSS colitis model, PSMA inhibition significantly reduced the disease activity index (FIG. 3). Moreover, the PSMA activity in the colonic and cecal mucosa of DSS-treated mice was potently inhibited by 2-PMPA, indicating target engagement (FIG. 4). 2-PMPA also significantly reduced spleen inflammation (FIG. 5) on mice with DSS-colitis, suggesting its immune-suppressive effect on systemic inflammation, in addition to gut inflammation.

Figure 6A:
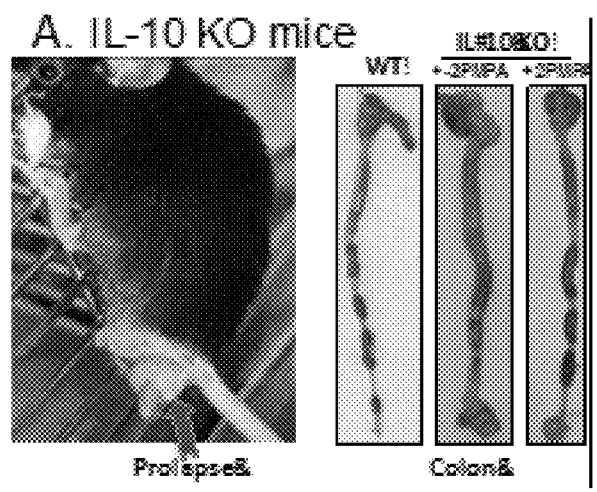
Figure 6B:
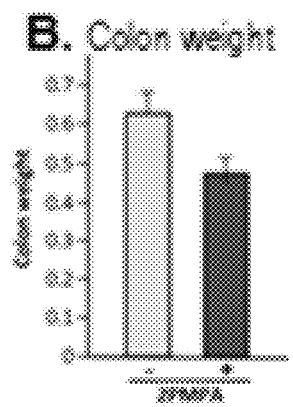
Figure 6C:
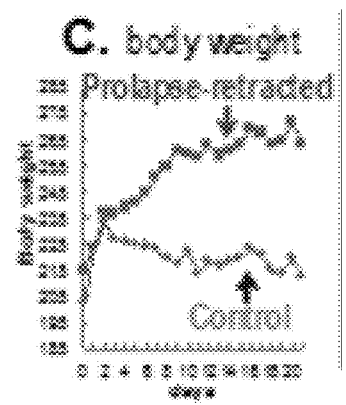
Figure 6D:
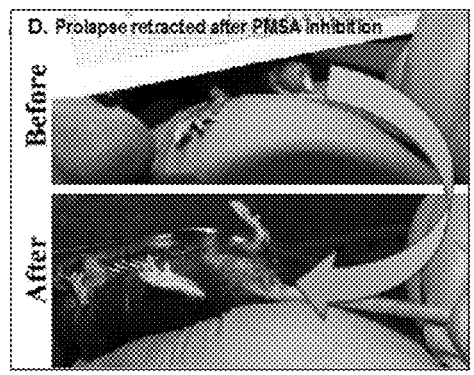

The efficacy of 2-PMPA in treatment of spontaneous colitis in IL-10 KO mice was also remarkable. 2-PMPA significantly reduced the disease severity, including macroscopic disease, colonic hypotrophy, and provided better stool consistency (FIGS. 6A-6B). More interestingly, a complete retraction of prolapse was observed in 2 of the 20 mice (10%) treated with the inhibitor (FIG. 6D), a phenomenon that has never been seen in more than 800 IL-10 KO mice used in previous efforts. The improvement of these prolapse-retracting mice was unequivocally obvious in that their body weight increased dramatically when compared to that of untreated control IL-10 KO mice (FIG. 6C). In conclusion, using three major animal models of IBD, the significance of PSMA as a novel therapeutic target for treatment of IBD was demonstrated.

Example 4

Two Structurally Distinct PSMA Inhibitors (E2072 and 2-PMPA) Show Similar Efficacy in IBD Models E2072 ((3-2-Mercaptoethyl)biphenyl-2,3-dicarboxylic acid, another PSMA inhibitor that is structurally distinct from 2-PMPA, exhibited similar ameliorating effects on DSS-induced colitis (FIG. 7).

Example 5

Oral Administration of TRIS POC 2-PMPA (Novel Prodrug of 2-PMPA) Exhibits Comparable Concentrations in Plasma and Colon to Those of 2-PMPA Given i.p.

2-PMPA demonstrated excellent efficacy following i.p. administration at 100 mg/kg in both the DSS and IL 10 knock out model (FIGS. 4 and 6). An orally bioavailable prodrug of 2-PMPA that enabled approximately 20 fold enhancement in permeability (FIG. 8A) in mice has now been identified. More importantly, the prodrug exhibits similar concentrations to 100 mg/kg i.p. administration when dosed p.o. FIG. 8A shows direct comparison of prodrug (30 mg/kg equiv) to 2-PMPA (100 mg/kg i.p.) in plasma and colon samples collected after 8 days of daily dosing in DSS mice. On day 8 the animals were sacrificed 2 h after dosing. The prodrug at a lower dose demonstrated comparable concentrations in both plasma and colon (approximately 15 µM at 30 mg/kg) compared to 2-PMPA (approximately 25 µM at 100 mg/kg).

Example 6

Oral Administration of TRIS POC 2-PMPA

Oral administration of TRIS POC 2-PMPA exhibited similar ameliorating effects on DSS-induced colitis, although a larger number of mice are needed in each experimental group to achieve statistical significance. As shown in FIG. 9, colon shortening (a signature of DSS-colitis) of DSS-colitis mice was reversed after oral administration of prodrug Tris POC 2-PMPA.

The presently disclosed genomic, clinical, and pharmacological data implicate PSMA in the etiology of inflammatory bowel disease (IBD). The data illustrate that PSMA enzymatic activity is consistently and robustly activated with the human clinical disease and that pharmacological inhibition of PSMA using multiple structurally distinct inhibitors ameliorate IBD symptoms.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Alex, P.; Zachos, N.C.; Nguyen, T.; Gonzales, L.; Chen, T. E.; Conklin, L. S.; Centola, M.; Li, X. Distinct cytokine patterns identified from multiplex profiles of murine DSS and TNBS-induced colitis. *Inflamm. Bowel Dis.* 2009, 15:341-352.

Alex, P.; Ye, M.; Zachos, N. Z.; Sipes, J.; Nguyen, T.; Suhodrev, M.; Gonzales, L.; Arora, Z.; Zhang, T.; Centola, M.; Guggino, S. E.; Li, X. Clc-5 Knockout mice exhibit novel immunomodulatory effects and are more susceptible to dextran sulphate sodium induced colitis. *J. Immunol.* 2010, 184:3988-3996.

Barditch-Crovo, P.; Deeks, S. G.; Collier, A.; Safrin, S.; Coakley, D. F.; Miller, M.; Kearney, B. P.; Coleman, R. L.; Lamy, P. D.; Kahn, J. O.; McGowan, I.; Lietman, P. S. Phase i/ii trial of the pharmacokinetics, safety, and antiretroviral activity of tenofovir disoproxil fumarate in human immunodeficiency virus-infected adults. *Antimicrob. Agents Chemother.* 2001, 45:2733-2739.

Barditch-Crovo, P.; Toole, J.; Hendrix, C. W.; Cundy, K. C.; Ebeling, D.; Jaffe, H. S.; Lietman, P. S. Anti-human immunodeficiency virus (HIV) activity, safety, and pharmacokinetics of adefovir dipivoxil (9-[2-(bis-pivaloyloxymethyl)-phosphonylmethoxyethyl]adenine) in HIV-infected patients. *J. Infect. Dis.* 1997, 176:406-413.

Colombel, J. F.; Sandborn, W. J.; Rutgeerts, P.; Enns, R.; Hanauer, S. B.; Panaccione, R.; Schreiber, S.; Byczkowski, D.; Li, J.; Kent, J. D.; Pollack, P. F., Adalimumab for maintenance of clinical response and remission in patients with Crohn's disease: the CHARM trial. *Gastroenterology* 2007, 132:52-65.

Cundy, K. C.; Sue, I. L.; Visor, G. C.; Marshburn, J.; Nakamura, C.; Lee, W. A.; Shaw, J. P. Oral formulations of adefovir dipivoxil: in vitro dissolution and in vivo bioavailability in dogs. *J. Pharm. Sci.* 1997, 86:1334-1338.

Glocker, E. O.; Kotlarz, D.; Klein, C.; Shah, C.; Grimbacher, B., IL-10 and IL-10 receptor defects in humans. *Ann. NY Acad. Sci.* 2011; 1246: 102-107.

Hamilton, M. J.; Snapper, S. B.; Blumberg, R. S., Update on biologic pathways in inflammatory bowel disease and their therapeutic relevance. *J. Gastroenterol.* 2012, 47:1-8.

Hanauer, S. B.; Feagan, B. G.; Lichtenstein, G. R.; Mayer, L. F.; Schreiber, S.; Colombel, J. F.; Rachmilewitz, D.; Wolf, D. C.; Olson, A.; Bao, W.; Rutgeerts, P., Maintenance infliximab for Crohn's disease: the ACCENT I randomised trial. *Lancet* 2002, 359:1541-1549.

Kaser, A.; Zeissig, S.; Blumberg, R. S., Inflammatory bowel disease. *Annu. Rev. Immunol.* 2010, 28:573-621.

Kirshner, B. S., Safety of azathioprine and 6-mercaptopurine in pediatric patients with inflammatory bowel disease. *Gastroenterology.* 1998, 115:813-821.

Kozuch, P. L. and Hanauer, S. B., Treatment of inflammatory bowel disease: A review of medical therapy. *World J. Gastroenterol.* 2008, 14:354-377.

Kühn, R.; Löhler, J.; Rennick, D.; Rajewsky, K.; Müller, W., Interleukin-10-deficient mice develop chronic enterocolitis. *Cell* 1993, 75: 263-74.

Lawrance, I. C. What is left when anti-tumour necrosis factor therapy in inflammatory bowel diseases fails? *World J. Gastroenterol.* 2014, 20:1248-1258.

Lupold, S. E.; Hicke, B. J.; Lin, Y.; and Coffey, D. S., Identification and characterization of nuclease-stabilized RNA molecules that bind human prostate cancer cells via the prostate-specific membrane antigen. *Cancer Res.* 2002, 62:4029-4033.

Mesters, J. R.; Barinka, C.; Li, W.; Tsukamoto, T.; Majer, P.; Slusher, B. S.; Konvalinka, J.; Hilgenfeld, R., Structure of glutamate carboxypeptidase II, a drug target in neuronal damage and prostate cancer. *EMBO J.* 2006, 25:1375-1384.

Rais, R.; Rojas, C.; Wozniak, K.; Wu, Y.; Zhao, M.; Tsukamoto, T.; Rudek, M. A.; Slusher, B. S., Bioanalytical method for evaluating the pharmacokinetics of the GCP-II inhibitor 2-phosphonomethyl pentanedioic acid (2-PMPA). *J. Pharm. Biomed. Anal.* 2014, 88:162-169; Epub Aug. 30, 2013.

Regueiro, M.; Siemanowski, B.; Kip, K. E.; Plevy, S., Infliximab dose intensification in Crohn's disease. *Inflamm. Bowel Dis.* 2007, 13:1093-1099.

Ristau, B. T.; O'Keefe, D. S.; Bacich, D. J., The prostate-specific membrane antigen: Lessons and current clinical implications from 20 years of research. *Urol. Oncol.* 2013, 32(3):272-9.

Robinson, M. B.; Blakely, R. D.; Couto, R.; Coyle, J. T., Hydrolysis of the brain dipeptide N-acetyl-L-aspartyl-L-glutamate. Identification and characterization of a novel N-acetylated alpha-linked acidic dipeptidase activity from rat brain. *J. Biol. Chem.* 1987, 262:14498-506.

Rojas, C.; Frazier, S. T.; Flanary, J.; Slusher, B. S., Kinetics and inhibition of glutamate carboxypeptidase II using a microplate assay. *Anal. Biochem.* 2002, 310: 50-4.

Rubin, E. and Farber, J. L., *Pathology* (Second Edition) Philadelphia: J. B. Lippincott Company, 1994.

Sartor, R. B., Mechanisms of disease: pathogenesis of Crohn's disease and ulcerative colitis. *Nat. Clin. Pract. Gastroenterol. Hepatol.* 2006, 3:390-407.

Schreiber, S.; Khaliq-Kareemi, M.; Lawrance, I. C.; Thomsen, O. O.; Hanauer, S. B.; McColm, J.; Bloomfield, R.; Sandborn, W. J., Maintenance therapy with certolizumab pegol for Crohn's disease. *N. Engl. J. Med.* 2007, 357: 239-250.

Schmidt, C.; Giese, T.; Hermann, E.; Zeuzem, S.; Meuer, S. C.; Stallmach, A., Predictive value of mucosal TNF-alpha transcripts in steroid-refractory Crohn's disease patients receiving intensive immunosuppressive therapy. *Inflamm. Bowel Dis.* 2007, 13:65-70.

Slusher, B. S.; Rojas, C.; Coyle, J. T., Glutamate Carboxypeptidase II. In: Rawlings and Salvesen, editors. Handbook for Proteolytic Enzymes, Academic Press. 3rd Edition. 2013, 1620-1626.

Strober, W.; Fuss, I.; and Mannon, P., The fundamental basis of inflammatory bowel disease. *J. Clin. Invest.* 2007, 117:514-521.

Tang H.; Brown M.; Ye Y.; Huang G.; Zhang Y.; Wang Y.; Zhai H.; Chen X.; Shen T. Y.; Tenniswood M., Prostate targeting ligands based on N-acetylated alpha-linked acidic dipeptidase. *Biochem. Biophys. Res. Commun.* 2003, 307:8-14.

Thackaberry, E. A. Vehicle selection for nonclinical oral safety studies. *Expert Opin. Drug Metab. Toxicol.* 2013, 9:1635-1646.

Van, A. G.; Van, R. M.; Sciot, R.; Dubois, B.; Vermeire, S.; Noman, M.; Verbeeck, J.; Geboes, K.; Robberecht, W.; Rutgeerts, P., Progressive multifocal leukoencephalopathy after natalizumab therapy for Crohn's disease. *N. Engl. J. Med.* 2005, 353:362-368.

Xavier, R. J. and Podolsky, D. K., Unravelling the pathogenesis of inflammatory bowel disease. *Nature* 2007, 448:427-434.

Zhang, T.; Song, B.; Zhu, W.; Xu, X.; Gong, Q. Q.; Morando, C.; Dassopoulos, T.; Newberry, R. D.; Hunt, S. R.; Li, E., An ileal Crohn's disease gene signature based on whole human genome expression profiles of disease unaffected ileal mucosal biopsies. *PLoS ONE* 2012; 7:e37139.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating an inflammatory bowel disease (IBD) in a subject in need thereof, the method comprising administering to the subject a therapeutically effective amount of a Prostate Specific Membrane Antigen (PSMA) inhibitor, wherein the PSMA inhibitor is in a neutral form or a salt form.

2. The method of claim 1, wherein the IBD is selected from the group consisting of Crohn's disease (CD) and ulcerative colitis (UC).

3. The method of claim 1, wherein the PSMA inhibitor is administered to the subject parenterally.

* * * * *